United States Patent [19]
Bandman et al.

[11] Patent Number: 5,965,369
[45] Date of Patent: Oct. 12, 1999

[54] HUMAN SUCCINYL-COENZYME A SYNTHETASE HOLOENZYME

[75] Inventors: Olga Bandman, Mountain View; Preeti Lal, Sunnyvale; Neil C. Corley; Chandra Patterson, both of Mountain View, all of Calif.

[73] Assignee: Incyte Pharmaceuticals, Inc., Palo Alto, Calif.

[21] Appl. No.: 09/099,677

[22] Filed: Jun. 18, 1998

[51] Int. Cl.$^6$ .............. C12Q 1/68; C12N 15/00; C12N 1/20; C07H 21/04

[52] U.S. Cl. .............. 435/6; 435/320.1; 435/325; 435/252.3; 536/23.2

[58] Field of Search .............. 435/183, 6, 320.1, 435/325, 252.3; 536/23.2

[56] References Cited

PUBLICATIONS

James et al., Biochimica et Biophysica Acta, 136, 169–176, 1997.
James et al., genbank Accesion No.: z68204, 1996.
Bridger, W.A. et al., "The Subunits of Succinyl–coenzyme A Synthetase—function and assembly", Biochem.Soc.Symp. 54:103–111 (1987).
Um, H.D. and Klein, C., "Evidence for Allosteric Regulation of Succinyl–CoA Synthetase", Biochem.J. 295:821–826 (1993).
Collier, G.E. and Nishimura, J.S., "Affinity Labeling of Succinyl–CoA Synthetase from Porcine Heart and *Escherichia coli* with Oxidized Coenzyme A Disulfide", J.Biol.Chem. 253:4938–4943 (1978).
Gougoux, A. et al., "Effect of Acetazolamide on Renal Metabolism and Ammoniagenesis in the Dog", Kidney Int. 31:1279–1290 (1987).
Ryan, D.G. et al., (GI 2258465), GenBank Sequence Database (Accession AF008588), National Center for Biotechnology Information, National Library of Medicine, Bethesda, Maryland 20894.
Bridger, W.A., (GI 164668), GenBank Sequence Database (Accession L06944), National Center for Biotechnology Information, National Library of Medicine, Bethesda, Maryland 20894.
Srere, P.A., "Citric Acid Cycle" *Methods in Enzymology* 13:3–11 (1969).

*Primary Examiner*—Robert A. Wax
*Assistant Examiner*—Maryam Monshipouri
*Attorney, Agent, or Firm*—Incyte Pharmaceuticals, Inc.

[57] ABSTRACT

The invention provides human succinyl-CoA synthetase holoenzyme (SCSH) and polynucleotides which identify and encode SCSH. The invention also provides expression vectors, host cells, antibodies, agonists, and antagonists. The invention also provides methods for diagnosing, treating or preventing disorders associated with expression of SCSH.

10 Claims, 4 Drawing Sheets

| | | |
|---|---|---|
| 211 | H Q T T Q V G L G Q S L C V G I G G D P F N G T D F I D C L | 2499773 |
| 198 | H Q T T Q V G L G Q S L C V G I G G D P F N G T D F T D C L | GI 2258465 |
| 241 | E I F L N D S A T E G I I L I G E I G G N A E E N A A A E F L | 2499773 |
| 228 | E I F L N D P A T E G I I L I G E I G G N A E E N A A A E F L | GI 2258465 |
| 271 | K Q H N S G P N S K P V V S F I A G L T A P P G R R M G H A | 2499773 |
| 258 | K Q H N S G P K S K P V V S F I A G L T A P P G R R M G H A | GI 2258465 |
| 301 | G A I I A G G K G G A K E K I S A L Q S A G V V V S M S P A | 2499773 |
| 288 | G A I I A G G K G G A K E K I T A L Q S A G V V V S M S P A | GI 2258465 |
| 331 | Q L G T T I Y K E F E K R K M L | 2499773 |
| 318 | Q L G T T I Y K E F E K R K M L | GI 2258465 |

| | | 3273853 |
|---|---|---|
| 211 | L G F V G P L K S Q A A D Q I T K L Y N L F L K I D A T Q V | 3273853 |
| 196 | L G F L G P L Q N Q A A D Q I K K L Y N L F L K I D A T Q V | GI 164669 |
| 241 | E V N P F G E T P E G Q V V C F D A K I N F D D N A E F R Q | 3273853 |
| 226 | E V N P F G E T P E G Q V V C F D A K I N F D D N A E F R Q | GI 164669 |
| 271 | K D I F A M D D K S E N E P I E N E A A K Y D L K Y I G L D | 3273853 |
| 256 | K D I F A M D D K S E N E P I E N E A A K Y D L K Y I G L D | GI 164669 |
| 301 | G N I A C F V N G A G L A M A T C D I I F L N G G K P A N F | 3273853 |
| 286 | G N I A C F V N G A G L A M A T C D I I F L N G G K P A N F | GI 164669 |
| 331 | L D L G G G V K E A Q V Y Q A F K L L T A D P K V E A I L V | 3273853 |
| 316 | L D L G G G V K E S Q V Y Q A F K L L T A D P K V E A I L V | GI 164669 |
| 361 | N I F G G I V N C A I I A N G I T K A C R E L E L K V P L V | 3273853 |
| 346 | N I F G G I V N C A I I A N G I T K A C R E L E L K V P L V | GI 164669 |
| 391 | V R L E G A N V Q E A Q K I L N N S G L P I T S A I D L E D | 3273853 |
| 376 | V R L E G T N V H E A Q N I L T N S G L P I T S A V D L E D | GI 164669 |
| 421 | A A K K A V A S V A K K | 3273853 |
| 406 | A A K K A V A S V T K K | GI 164669 |

FIGURE 2B

```
                    SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
          (A) LENGTH: 346 amino acids
          (B) TYPE: amino acid
          (C) STRANDEDNESS: single
          (D) TOPOLOGY: linear (vii) IMMEDIATE SOURCE:
          (A) LIBRARY: ADRETUT05
          (B) CLONE: 2499773

(xi) SEQUENCE DESCRIPTION: SEQ ID NO: 1:

Met Thr Ala Thr Leu Ala Ala Ala Ala Asp Ile Ala Thr Met Val
                  5                  10                  15

Ser Gly Ser Ser Gly Leu Ala Ala Ala Arg Leu Leu Ser Arg Ser
                 20                  25                  30

Phe Leu Leu Pro Gln Asn Gly Ile Arg His Cys Ser Tyr Thr Ala
                 35                  40                  45

Ser Arg Gln His Leu Tyr Val Asp Lys Asn Thr Lys Ile Ile Cys
                 50                  55                  60

Gln Gly Phe Thr Gly Lys Gln Gly Thr Phe His Ser Gln Gln Ala
                 65                  70                  75

Leu Glu Tyr Gly Thr Lys Leu Val Gly Gly Thr Thr Pro Gly Lys
                 80                  85                  90

Gly Gly Gln Thr His Leu Gly Leu Pro Val Phe Asn Thr Val Lys
                 95                 100                 105

Glu Ala Lys Glu Gln Thr Gly Ala Thr Ala Ser Val Ile Tyr Val
                110                 115                 120

Pro Pro Pro Phe Ala Ala Ala Ala Ile Asn Glu Ala Ile Glu Ala
                125                 130                 135

Glu Ile Pro Leu Val Val Cys Ile Thr Glu Gly Ile Pro Gln Gln
                140                 145                 150
```

```
Asp Met Val Arg Val Lys His Lys Leu Leu Arg Gln Glu Lys Thr
            155                 160                 165
Arg Leu Ile Gly Pro Asn Cys Pro Gly Val Ile Asn Pro Gly Glu
            170                 175                 180
Cys Lys Ile Gly Ile Met Pro Gly His Ile His Lys Lys Gly Arg
            185                 190                 195
Ile Gly Ile Val Ser Arg Ser Gly Thr Leu Thr Tyr Glu Ala Val
            200                 205                 210
His Gln Thr Thr Gln Val Gly Leu Gly Gln Ser Leu Cys Val Gly
            215                 220                 225
Ile Gly Gly Asp Pro Phe Asn Gly Thr Asp Phe Ile Asp Cys Leu
            230                 235                 240
Glu Ile Phe Leu Asn Asp Ser Ala Thr Glu Gly Ile Ile Leu Ile
            245                 250                 255
Gly Glu Ile Gly Gly Asn Ala Glu Glu Asn Ala Ala Glu Phe Leu
            260                 265                 270
Lys Gln His Asn Ser Gly Pro Asn Ser Lys Pro Val Val Ser Phe
            275                 280                 285
Ile Ala Gly Leu Thr Ala Pro Pro Gly Arg Arg Met Gly His Ala
            290                 295                 300
Gly Ala Ile Ile Ala Gly Gly Lys Gly Gly Ala Lys Glu Lys Ile
            305                 310                 315
Ser Ala Leu Gln Ser Ala Gly Val Val Val Ser Met Ser Pro Ala
            320                 325                 330
Gln Leu Gly Thr Thr Ile Tyr Lys Glu Phe Glu Lys Arg Lys Met
            335                 340                 345
Leu
```

(2) INFORMATION FOR SEQ ID NO: 2:

(i) SEQUENCE CHARACTERISTICS:
        (A) LENGTH: 1274 base pairs
        (B) TYPE: nucleic acid
        (C) STRANDEDNESS: single
        (D) TOPOLOGY: linear (vii) IMMEDIATE SOURCE:
        (A) LIBRARY: ADRETUT05
        (B) CLONE: 2499773

(xi) SEQUENCE DESCRIPTION: SEQ ID NO: 2:

```
TTGGCGTATG ACCGCAACCC TTGCCGCTGC CGCTGACATC GCTACCATGG TCTCCGGCAG      60

CAGCGGCCTC GCCGCCGCCC GTCTCCTGTC GCGCAGCTTC CTCCTGCCGC AGAATGGAAT     120

TCGGCATTGT TCCTACACAG CTTCTCGGCA ACATCTCTAT GTTGATAAAA ATACAAAGAT     180

TATTTGCCAG GGTTTCACTG GCAAACAGGG CACCTTTCAC AGCCAGCAGG CATTGGAATA     240

TGGCACCAAA CTCGTTGGAG GAACCACTCC AGGGAAAGGA GGCCAGACAC ATCTGGGCTT     300

ACCTGTCTTT AATACTGTGA AGGAGGCCAA AGAACAGACA GGAGCAACGG CTTCTGTCAT     360

TTATGTTCCT CCGCCTTTTG CTGCTGCTGC CATTAATGAA GCTATTGAGG CAGAAATTCC     420

CTTGGTTGTG TGTATCACTG AAGGAATTCC CCAGCAGGAC ATGGTACGAG TCAAGCACAA     480

ACTGCTGCGC CAGGAAAAGA CAAGGCTAAT TGGGCCCAAC TGCCCTGGAG TCATCAATCC     540

TGGAGAATGT AAAATTGGCA TCATGCCTGG CCATATTCAC AAAAAAGGAA GGATTGGCAT     600

TGTGTCCAGA TCTGGCACCC TGACTTATGA AGCAGTTCAC CAAACAACGC AAGTTGGATT     660

GGGGCAGTCT TTGTGCGTTG GCATTGGAGG TGATCCTTTT AATGGAACAG ATTTTATTGA     720
```

```
CTGCCTCGAA ATCTTTTTGA ACGATTCTGC CACAGAAGGC ATCATATTGA TTGGTGAAAT    780

TGGTGGTAAT GCAGAAGAGA ATGCTGCAGA ATTTTTGAAG CAACATAATT CAGGTCCAAA    840

TTCCAAGCCT GTAGTGTCCT TCATTGCTGG TTTAACTGCT CCTCCTGGGA AGAATGGG     900

TCATGCCGGG GCAATTATTG CTGGAGGAAA AGGTGGAGCT AAAGAGAAGA TCTCTGCCCT    960

TCAGAGTGCA GGAGTTGTGG TCAGTATGTC TCCTGCACAG CTGGGAACCA CGATCTACAA   1020

GGAATTTGAA AAGAGGAAGA TGCTATGAAA GAAAAAAAAA ATTCCTAAAA CTGTGGAATG   1080

GATCACGTAG ACATGTAACC CAGCAGCAGT TTGCTTCTGT TGTCCACTGA TTAATCAGCC   1140

TATGTGCCTG ACACTGGTCT TGCAGTACAA CTGGAAGCCA AAACAAGGTG GAAGATGTCC   1200

TGAATTAAGA CGTTTTCACC ACATTGTATT ACAGAGACAG CCAATAAATC TACTATTTGA   1260

TTTCAAAAAA AAAA                                                   1274
```

(2) INFORMATION FOR SEQ ID NO: 3:

(i) SEQUENCE CHARACTERISTICS:
        (A) LENGTH: 432 amino acids
        (B) TYPE: amino acid
        (C) STRANDEDNESS: single
        (D) TOPOLOGY: linear (vii) IMMEDIATE SOURCE:
        (A) LIBRARY: PROSBPT06
        (B) CLONE: 3273853

(xi) SEQUENCE DESCRIPTION: SEQ ID NO: 3:

```
Met Ala Ser Pro Val Ala Ala Gln Ala Gly Lys Leu Leu Arg Ala
                 5                  10                  15
Leu Ala Leu Arg Pro Arg Phe Leu Ala Ala Gly Ser Gln Ala Val
             20                  25                  30
Gln Leu Thr Ser Arg Arg Trp Leu Asn Leu Gln Glu Tyr Gln Ser
             35                  40                  45
Lys Lys Leu Met Ser Asp Asn Gly Val Arg Val Gln Arg Phe Phe
             50                  55                  60
Val Ala Asp Thr Ala Asn Glu Ala Leu Glu Ala Ala Lys Arg Leu
             65                  70                  75
Asn Ala Lys Glu Ile Val Leu Lys Ala Gln Ile Leu Ala Gly Gly
             80                  85                  90
Arg Gly Lys Gly Val Phe Asn Ser Gly Leu Lys Gly Gly Val His
             95                 100                 105
Leu Thr Lys Asp Pro Asn Val Val Gly Gln Leu Ala Lys Gln Met
            110                 115                 120
Ile Gly Tyr Asn Leu Ala Thr Lys Gln Thr Pro Lys Glu Gly Val
            125                 130                 135
Lys Val Asn Lys Val Met Val Ala Glu Ala Leu Asp Ile Ser Arg
            140                 145                 150
Glu Thr Tyr Leu Ala Ile Leu Met Asp Arg Ser Cys Asn Gly Pro
            155                 160                 165
Val Leu Val Gly Gln Pro Gln Gly Gly Val Asp Ile Glu Glu Val
            170                 175                 180
Ala Ala Ser Asn Pro Glu Leu Ile Phe Lys Glu Gln Ile Asp Ile
            185                 190                 195
Phe Glu Gly Ile Lys Asp Ser Gln Ala Gln Arg Met Ala Glu Asn
            200                 205                 210
Leu Gly Phe Val Gly Pro Leu Lys Ser Gln Ala Ala Asp Gln Ile
            215                 220                 225
```

```
Thr Lys Leu Tyr Asn Leu Phe Leu Lys Ile Asp Ala Thr Gln Val
            230                 235                 240
Glu Val Asn Pro Phe Gly Glu Thr Pro Glu Gly Gln Val Val Cys
            245                 250                 255
Phe Asp Ala Lys Ile Asn Phe Asp Asp Asn Ala Glu Phe Arg Gln
            260                 265                 270
Lys Asp Ile Phe Ala Met Asp Asp Lys Ser Glu Asn Glu Pro Ile
            275                 280                 285
Glu Asn Glu Ala Ala Lys Tyr Asp Leu Lys Tyr Ile Gly Leu Asp
            290                 295                 300
Gly Asn Ile Ala Cys Phe Val Asn Gly Ala Gly Leu Ala Met Ala
            305                 310                 315
Thr Cys Asp Ile Ile Phe Leu Asn Gly Gly Lys Pro Ala Asn Phe
            320                 325                 330
Leu Asp Leu Gly Gly Gly Val Lys Glu Ala Gln Val Tyr Gln Ala
            335                 340                 345
Phe Lys Leu Leu Thr Ala Asp Pro Lys Val Glu Ala Ile Leu Val
            350                 355                 360
Asn Ile Phe Gly Gly Ile Val Asn Cys Ala Ile Ile Ala Asn Gly
            365                 370                 375
Ile Thr Lys Ala Cys Arg Glu Leu Glu Leu Lys Val Pro Leu Val
            380                 385                 390
Val Arg Leu Glu Gly Ala Asn Val Gln Glu Ala Gln Lys Ile Leu
            395                 400                 405
Asn Asn Ser Gly Leu Pro Ile Thr Ser Ala Ile Asp Leu Glu Asp
            410                 415                 420
Ala Ala Lys Lys Ala Val Ala Ser Val Ala Lys Lys
            425                 430

(2) INFORMATION FOR SEQ ID NO: 4:

(i) SEQUENCE CHARACTERISTICS:
        (A) LENGTH: 1700 base pairs
        (B) TYPE: nucleic acid
        (C) STRANDEDNESS: single
        (D) TOPOLOGY: linear (vii) IMMEDIATE SOURCE:
        (A) LIBRARY: PROSBPT06
        (B) CLONE: 3273853

(xi) SEQUENCE DESCRIPTION: SEQ ID NO: 4:

CGAGTTTCCT GTTTAAGATG GCGTCCCCCG TAGCAGCGCA GGCCGGGAAG CTTCTGCGAG      60

CCCTAGCGCT GCGGCCCCGC TTCCTGGCGG CCGGGTCCCA GGCAGTTCAA TTAACCTCCA     120

GAAGATGGCT GAACCTGCAG GAATACCAGA GCAAGAAACT GATGTCTGAC AACGGAGTGA     180

GAGTTCAAAG ATTCTTTGTA GCAGACACTG CAAATGAAGC TCTCGAGGCT GCTAAGAGAC     240

TAAATGCAAA AGAAATTGTT TTAAAAGCCC AGATCTTAGC TGGAGGAAGA GGAAAAGGTG     300

TCTTCAATAG TGGTTTGAAA GGAGGTGTTC ATTTAACAAA AGACCCTAAT GTTGTGGGAC     360

AGCTGGCTAA ACAGATGATT GGGTACAATC TAGCGACAAA ACAAACTCCA AAAGAAGGTG     420

TGAAAGTTAA CAAGGTGATG GTTGCTGAAG CCTTGGATAT TTCCAGAGAA ACCTACCTGG     480

CAATTCTGAT GGACCGGTCC TGCAATGGCC CCGTGCTGGT GGGGCAGCCC AGGGGGGCG      540

TCGACATTGA AGAGGTGGCT GCTTCAAACC CGGAGCTCAT TTTTAAGGAG CAAATTGACA     600

TTTTTGAAGG AATAAAGGAC AGCCAAGCTC AGCGGATGGC CGAAAATCTA GGCTTCGTTG     660
```

-continued

```
GGCCTTTGAA AAGCCAGGCT GCAGATCAAA TTACGAAGCT GTATAATCTC TTCCTGAAAA        720

TTGATGCTAC TCAGGTGGAA GTGAATCCCT TTGGTGAAAC TCCAGAAGGA CAAGTTGTCT        780

GTTTTGATGC AAGATAAAC TTTGATGACA ACGCAGAATT CCGACAAAAA GACATATTTG         840

CTATGGACGA CAAATCAGAG AATGAGCCCA TTGAAAATGA AGCTGCCAAA TATGATCTAA        900

AATACATAGG ACTAGATGGG AACATTGCCT GCTTTGTGAA TGGTGCTGGG CTCGCCATGG        960

CTACTTGTGA TATCATTTTC CTTAATGGTG GGAAGCCAGC CAACTTCTTG GATCTTGGAG       1020

GTGGTGTAAA GGAAGCTCAA GTATATCAAG CATTCAAATT GCTCACAGCT GATCCTAAGG       1080

TTGAAGCCAT CCTTGTCAAT ATATTTGGTG GTATCGTCAA CTGTGCCATC ATTGCCAATG       1140

GGATCACCAA AGCCTGCCGG GAGCTAGAAC TCAAGGTGCC CCTGGTGGTC CGGCTTGAAG       1200

GAGCCAACGT CCAAGAGGCC CAGAAGATAC TCAACAACAG CGGACTCCCC ATTACTTCAG       1260

CCATTGACCT GGAGGATGCA GCCAAGAAGG CTGTGGCCAG TGTGGCCAAG AAGTGATGTC       1320

TTTGTCCTGA TCCAATGGAG AAAGAAAGCC ATTTTTCCGT AAAAAGGGAT GGTTCATCAT       1380

TGTGAAAGAA ATGGTTATCT CATTGGGGAA GAAAAGGGGA GGGGGAAGGC AAGAATCACT       1440

GAAAAATCTT AAATCTGTGT TTTCTGGAAT AAGATATCTA GACAGCCTAA ATCTGATTTT       1500

GGTCTTTATA AAATAATAT ATTGTGTTCT CATACTTTTC TGTCACTGTA AGCCTGCCCA       1560

GTAGGCAGTG TTTTGCAGAC TTTGGGGAGT GGTCTATGTG GCCAAATATT GTGTGTATAG       1620

ACAGAATTTG AAATCAAGTC CTGCNTCANT TACAAGAATT TTGGTGGGCA TCGAATCCNA       1680

CANAATGAAA AAGAAAAACA                                                    1700
```

(2) INFORMATION FOR SEQ ID NO: 5:

(i) SEQUENCE CHARACTERISTICS:
        (A) LENGTH: 333 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: g2258465

(xi) SEQUENCE DESCRIPTION: SEQ ID NO: 5:

```
Met Ala Ser Gly Ser Ser Gly Leu Ala Ala Arg Leu Leu Ser Arg
 1               5                  10                  15

Ser Phe Leu Leu Gln Gln Asn Gly Ile Arg His Cys Ser Tyr Thr Ala
                20                  25                  30

Ser Arg Lys His Leu Tyr Val Asp Lys Asn Thr Lys Val Ile Cys Gln
            35                  40                  45

Gly Phe Thr Gly Lys Gln Gly Thr Phe His Ser Gln Gln Ala Leu Glu
        50                  55                  60

Tyr Gly Thr Asn Leu Val Gly Gly Thr Thr Pro Gly Lys Gly Gly Lys
65                  70                  75                  80

Thr His Leu Gly Leu Pro Val Phe Asn Thr Val Lys Glu Ala Lys Glu
                85                  90                  95

Gln Thr Gly Ala Thr Ala Ser Val Ile Tyr Val Pro Pro Pro Phe Ala
            100                 105                 110

Ala Ala Ile Asn Glu Ala Ile Asp Ala Glu Val Pro Leu Val Val
            115                 120                 125

Cys Ile Thr Glu Gly Ile Pro Gln Gln Asp Met Val Arg Val Lys His
            130                 135                 140

Arg Leu Leu Arg Gln Gly Lys Thr Arg Leu Ile Gly Pro Asn Cys Pro
145                 150                 155                 160
```

Gly Val Ile Asn Pro Gly Glu Cys Lys Ile Gly Ile Met Pro Gly His
                165                 170                 175

Ile His Lys Lys Gly Arg Ile Gly Ile Val Ser Arg Ser Gly Thr Leu
                180                 185                 190

Thr Tyr Glu Ala Val His Gln Thr Thr Gln Val Gly Leu Gly Gln Ser
                195                 200                 205

Leu Cys Val Gly Ile Gly Gly Asp Pro Phe Asn Gly Thr Asp Phe Thr
                210                 215                 220

Asp Cys Leu Glu Ile Phe Leu Asn Asp Pro Ala Thr Glu Gly Ile Ile
225                 230                 235                 240

Leu Ile Gly Glu Ile Gly Gly Asn Ala Glu Glu Asn Ala Ala Glu Phe
                245                 250                 255

Leu Lys Gln His Asn Ser Gly Pro Lys Ser Lys Pro Val Val Ser Phe
                260                 265                 270

Ile Ala Gly Leu Thr Ala Pro Pro Gly Arg Arg Met Gly His Ala Gly
                275                 280                 285

Ala Ile Ile Ala Gly Gly Lys Gly Gly Ala Lys Glu Lys Ile Thr Ala
                290                 295                 300

Leu Gln Ser Ala Gly Val Val Ser Met Ser Pro Ala Gln Leu Gly
305                 310                 315                 320

Thr Thr Ile Tyr Lys Glu Phe Glu Lys Arg Lys Met Leu
                325                 330

(2) INFORMATION FOR SEQ ID NO: 6:

(i) SEQUENCE CHARACTERISTICS:
        (A) LENGTH: 417 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: g164669

(xi) SEQUENCE DESCRIPTION: SEQ ID NO: 6:

Leu Ala Phe Arg Pro Pro Leu Leu Ala Ala Arg Ser Gln Val Val
                 5                  10                  15

Gln Leu Thr Pro Arg Arg Trp Leu Asn Leu Gln Glu Tyr Gln Ser
                20                  25                  30

Lys Lys Leu Met Ser Asp Asn Gly Val Lys Val Gln Arg Phe Phe
                35                  40                  45

Val Ala Asp Thr Ala Asn Glu Ala Leu Glu Ala Ala Lys Arg Leu
                50                  55                  60

Asn Ala Lys Glu Ile Val Leu Lys Ala Gln Ile Leu Ala Gly Gly
                65                  70                  75

Arg Gly Lys Gly Val Phe Ser Ser Gly Leu Lys Gly Gly Val His
                80                  85                  90

Leu Thr Lys Asp Pro Glu Val Val Gly Gln Leu Ala Lys Gln Met
                95                  100                 105

Ile Gly Tyr Asn Leu Ala Thr Lys Gln Thr Pro Lys Glu Gly Val
                110                 115                 120

Lys Val Asn Lys Val Met Val Ala Glu Ala Leu Asp Ile Ser Arg
                125                 130                 135

Glu Thr Tyr Leu Ala Ile Leu Met Asp Arg Ser Cys Asn Gly Pro
                140                 145                 150

Val Leu Val Gly Ser Pro Gln Gly Gly Val Asp Ile Glu Glu Val

-continued

```
            155                 160                 165
Ala Ala Ser Asn Pro Glu Leu Ile Phe Lys Glu Gln Ile Asp Ile
                170                 175                 180
Ile Glu Gly Ile Lys Asp Ser Gln Ala Gln Arg Met Ala Glu Asn
                185                 190                 195
Leu Gly Phe Leu Gly Pro Leu Gln Asn Gln Ala Ala Asp Gln Ile
                200                 205                 210
Lys Lys Leu Tyr Asn Leu Phe Leu Lys Ile Asp Ala Thr Gln Val
                215                 220                 225
Glu Val Asn Pro Phe Gly Glu Thr Pro Glu Gly Gln Val Val Cys
                230                 235                 240
Phe Asp Ala Lys Ile Asn Phe Asp Asp Asn Ala Glu Phe Arg Gln
                245                 250                 255
Lys Asp Ile Phe Ala Met Asp Asp Lys Ser Glu Asn Glu Pro Ile
                260                 265                 270
Glu Asn Glu Ala Ala Lys Tyr Asp Leu Lys Tyr Ile Gly Leu Asp
                275                 280                 285
Gly Asn Ile Ala Cys Phe Val Asn Gly Ala Gly Leu Ala Met Ala
                290                 295                 300
Thr Cys Asp Ile Ile Phe Leu Asn Gly Gly Lys Pro Ala Asn Phe
                305                 310                 315
Leu Asp Leu Gly Gly Val Lys Glu Ser Gln Val Tyr Gln Ala
                320                 325                 330
Phe Lys Leu Leu Thr Ala Asp Pro Lys Val Glu Ala Ile Leu Val
                335                 340                 345
Asn Ile Phe Gly Gly Ile Val Asn Cys Ala Ile Ile Ala Asn Gly
                350                 355                 360
Ile Thr Lys Ala Cys Arg Glu Leu Glu Leu Lys Val Pro Leu Val
                365                 370                 375
Val Arg Leu Glu Gly Thr Asn Val His Glu Ala Gln Asn Ile Leu
                380                 385                 390
Thr Asn Ser Gly Leu Pro Ile Thr Ser Ala Val Asp Leu Glu Asp
                395                 400                 405
Ala Ala Lys Lys Ala Val Ala Ser Val Thr Lys Lys
                410                 415
```

HUMAN SUCCINYL-COENZYME A SYNTHETASE HOLOENZYME

FIELD OF THE INVENTION

This invention relates to nucleic acid and amino acid sequences of human succinyl-coenzyme A synthetase holoenzyme and to the use of these sequences in the diagnosis, treatment, and prevention of neoplastic, reproductive, immunological, vesicle trafficking, and nervous disorders.

BACKGROUND OF THE INVENTION

Mammalian mitochondrial succinyl-coenzyme A (CoA) synthetase holoenzyme (SCS; EC 6.2.1.4) is a component of the tricarboxylic acid cycle that catalyzes the formation of succinate from succinyl-CoA and the formation of GTP from GDP and phosphate within the mitochondrial matrix. Succinyl-CoA is the product of $NAD^+$-dependant oxidative decarboxylation of $\alpha$-ketoglutarate and CoA. In the reverse reaction, succinyl-CoA is decomposed to succinate, CoASH, GDP, and inorganic phosphate by succinyl-CoA ligase (GDP-forming). The SCS holoenzyme is a dimer made up of one $\alpha$ subunit and one $\beta$ subunit. (Bridger, W. A. et al. (1987) Biochem. Soc. Symp. 54:103–111.) Sequence analysis of the cDNAs encoding succinyl-CoA synthetase subunits and succinyl-CoA ligase subunits shows that both enzymes are encoded by the same $\alpha$ subunit and $\beta$ subunit genes.

Post-translational covalent modification of enzymes can activate or inactivate enzyme activity. SCS activity purified from the slime mold *Dictyostelium discoidium* is regulated by ATP- and GTP-dependant phosphorylation of the $\alpha$ subunit. Phosphorylation of the $\alpha$ subunit is stimulated by low concentrations of GDP, and this appears to correlate with regulation of SCS activity at an allosteric binding site. (Um, H. D. and Klein, C. (1993) 295:821–826.) The $\beta$ subunit binds CoASH through a disulphide bond to a sulphydryl group of the $\beta$ subunit. (Collier, G. E. and Nishimura, J. S. (1978) J. Biol. Chem. 253:4938–4943.)

In addition to the activity of SCS in the tricarboxylic acid pathway, SCS activity has been reported in amino acid metabolic pathways. Valine, methionine, and isoleucine are catabolized in a series of enzyme-catalyzed reactions to succinyl-CoA. Biochemical intermediates and enzymes include methacrylyl-CoA, 3-hydroxyisobutyryl-CoA, propionyl CoA carboxylase, hydroxyisobutyric acid, and methylmalonyl CoA mutase. Methylmalonyl CoA mutase activity limits intracellular levels of succinyl-CoA and has been associated with several inherited disorders including methylmalonic aciduria. Methylmalonyl CoA mutase also participates in the oxidation of fatty acids that have an odd number of carbon atoms.

Condensation of succinyl-CoA and glycine to form $\delta$-aminolevulinate is the first step of porphyrin biosynthesis. Aberrant succinyl-CoA metabolism may result in clinical symptoms such as dermal photosensitivity and anaemia. Acetazolamide is commonly used in the control of fluid secretion, in particular as an adjunctive treatment for edema due to congestive heart failure, seizures, glaucoma, and to prevent or ameliorate the symptoms associated with acute altitude sickness. SCS activity in the kidney enables ammonia to be excreted in urine, and this activity is inhibited by acetazolamide. (Gougour, A. et al. (1987) Kidney Int. 31:1279–1290.)

The discovery of a new human succinyl-coenzyme A synthetase holoenzyme and the polynucleotides encoding it satisfies a need in the art by providing new compositions which are useful in the diagnosis, treatment, and prevention of neoplastic, reproductive, immunological, vesicle trafficking, and nervous disorders.

SUMMARY OF THE INVENTION

The invention features two substantially purified polypeptides, human succinyl-CoA synthetase holoenzyme, referred to collectively as "SCSH" and individually as "SCSH-1" and "SCSH-2." In one aspect, the invention provides a substantially purified polypeptide comprising an amino acid sequence selected from the group consisting of SEQ ID NO:1, SEQ ID NO:3, a fragment of SEQ ID NO:1, and a fragment of SEQ ID NO:3.

The invention further provides a substantially purified variant having at least 90% amino acid identity to the amino acid sequences of SEQ ID NO:1 or SEQ ID NO:3, or to a fragment of either of these sequences. The invention also provides an isolated and purified polynucleotide encoding the polypeptide comprising an amino acid sequence selected from the group consisting of SEQ ID NO:1, SEQ ID NO:3, a fragment of SEQ ID NO:1, and a fragment of SEQ ID NO:3. The invention also includes an isolated and purified polynucleotide variant having at least 85% polynucleotide sequence identity to the polynucleotide encoding the polypeptide comprising an amino acid sequence selected from the group consisting of SEQ ID NO:1, SEQ ID NO:3, a fragment of SEQ ID NO:1, and a fragment of SEQ ID NO:3.

Additionally, the invention provides an isolated and purified polynucleotide which hybridizes under stringent conditions to the polynucleotide encoding the polypeptide comprising an amino acid sequence selected from the group consisting of SEQ ID NO:1, SEQ ID NO:3, a fragment of SEQ ID NO:1, and a fragment of SEQ ID NO:3, as well as an isolated and purified polynucleotide having a sequence which is complementary to the polynucleotide encoding the polypeptide comprising the amino acid sequence selected from the group consisting of SEQ ID NO:1, SEQ ID NO:3, a fragment of SEQ ID NO:1, and a fragment of SEQ ID NO:3.

The invention also provides an isolated and purified polynucleotide comprising a polynucleotide sequence selected from the group consisting of SEQ ID NO:2, SEQ ID NO:4, a fragment of SEQ ID NO:2, and a fragment of SEQ ID NO:4. The invention further provides an isolated and purified polynucleotide variant having at least 85% polynucleotide sequence identity to the polynucleotide sequence comprising a polynucleotide sequence selected from the group consisting of SEQ ID NO:2, SEQ ID NO:4, a fragment of SEQ ID NO:2, and a fragment of SEQ ID NO:4, as well as an isolated and purified polynucleotide having a sequence which is complementary to the polynucleotide comprising a polynucleotide sequence selected from the group consisting of SEQ ID NO:2, SEQ ID NO:4, a fragment of SEQ ID NO:2, and a fragment of SEQ ID NO:4.

The invention further provides an expression vector containing at least a fragment of the polynucleotide encoding the polypeptide comprising an amino acid sequence selected from the group consisting of SEQ ID NO:1, SEQ ID NO:3, a fragment of SEQ ID NO:1, and a fragment of SEQ ID NO:3. In another aspect, the expression vector is contained within a host cell.

The invention also provides a method for producing a polypeptide comprising the amino acid sequence selected from the group consisting of SEQ ID NO:1, SEQ ID NO:3, a fragment of SEQ ID NO:1, and a fragment of SEQ ID NO:3, the method comprising the steps of: (a) culturing the host cell containing an expression vector containing at least a fragment of a polynucleotide encoding the polypeptide under conditions suitable for the expression of the polypeptide; and (b) recovering the polypeptide from the host cell culture.

The invention also provides a pharmaceutical composition comprising a substantially purified polypeptide having the amino acid sequence selected from the group consisting of SEQ ID NO:1, SEQ ID NO:3, a fragment of SEQ ID NO:1, and a fragment of SEQ ID NO:3 in conjunction with a suitable pharmaceutical carrier.

The invention further includes a purified antibody which binds to a polypeptide comprising the amino acid sequence selected from the group consisting of SEQ ID NO:1, SEQ ID NO:3, a fragment of SEQ ID NO:1, and a fragment of SEQ ID NO:3, as well as a purified agonist and a purified antagonist to the polypeptide.

The invention also provides a method for treating or preventing a neoplastic disorder, the method comprising administering to a subject in need of such treatment an effective amount of an antagonist of the polypeptide having an amino acid sequence selected from the group consisting of SEQ ID NO:1, SEQ ID NO:3, a fragment of SEQ ID NO:1, and a fragment of SEQ ID NO:3.

The invention also provides a method for treating or preventing a reproductive disorder the method comprising administering to a subject in need of such treatment an effective amount of an antagonist of the polypeptide having an amino acid sequence selected from the group consisting of SEQ ID NO:1, SEQ ID NO:3, a fragment of SEQ ID NO:1, and a fragment of SEQ ID NO:3.

The invention also provides a method for treating or preventing an immunological disorder, the method comprising administering to a subject in need of such treatment an effective amount of an antagonist of the polypeptide having an amino acid sequence selected from the group consisting of SEQ ID NO:1, SEQ ID NO:3, a fragment of SEQ ID NO:1, and a fragment of SEQ ID NO:3.

The invention also provides a method for treating or preventing a vesicle trafficking disorder, the method comprising administering to a subject in need of such treatment an effective amount of an antagonist of the polypeptide having an amino acid sequence selected from the group consisting of SEQ ID NO:1, SEQ ID NO:3, a fragment of SEQ ID NO:1, and a fragment of SEQ ID NO:3.

The invention also provides a method for treating or preventing a nervous disorder, the method comprising administering to a subject in need of such treatment an effective amount of an antagonist of the polypeptide having an amino acid sequence selected from the group consisting of SEQ ID NO:1, SEQ ID NO:3, a fragment of SEQ ID NO:1, and a fragment of SEQ ID NO:3.

The invention also provides a method for detecting a polynucleotide encoding the polypeptide comprising the amino acid sequence selected from the group consisting of SEQ ID NO:1, SEQ ID NO:3, a fragment of SEQ ID NO:1, and a fragment of SEQ ID NO:3 in a biological sample containing nucleic acids, the method comprising the steps of: (a) hybridizing the complement of the polynucleotide sequence encoding the polypeptide comprising the amino acid sequence selected from the group consisting of SEQ ID NO:1, SEQ ID NO:3, a fragment of SEQ ID NO:1, and a fragment of SEQ ID NO:3 to at least one of the nucleic acids of the biological sample, thereby forming a hybridization complex; and (b) detecting the hybridization complex, wherein the presence of the hybridization complex correlates with the presence of a polynucleotide encoding the polypeptide in the biological sample. In one aspect, the method further comprises amplifying the polynucleotide prior to hybridization.

BRIEF DESCRIPTION OF THE FIGURES

FIGS. 1A and 1B show the amino acid sequence alignments between SCSH-1 (2499773; SEQ ID NO:1) and pig SCS α subunit (GI 2258465; SEQ ID NO:5), produced using the multisequence alignment program of LASERGENE software (DNASTAR Inc, Madison Wis.).

FIGS. 2A and 2B show the amino acid sequence alignments between SCSH-2 (3273853; SEQ ID NO:3) and pig SCS β subunit (GI 164669; SEQ ID NO:6), produced using the multisequence alignment program of LASERGENE software.

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

Definitions

"SCSH," as used herein, refers to the amino acid sequences, or variant thereof, of substantially purified SCSH obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to SCSH, increases or prolongs the duration of the effect of SCSH. Agonists may include proteins, nucleic acids, carbohydrates, or any other molecules which bind to and modulate the effect of SCSH.

An "allelic variant," as this term is used herein, is an alternative form of the gene encoding SCSH. Allelic variants may result from at least one mutation in the nucleic acid sequence and may result in altered mRNAs or in polypeptides whose structure or function may or may not be altered.

Any given natural or recombinant gene may have none, one, or many allelic forms. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding SCSH, as described herein, include those sequences with deletions, insertions, or substitutions of different nucleotides, resulting in a polynucleotide the same as SCSH or a polypeptide with at least one functional characteristic of SCSH. Included within this definition are polymorphisms which may or may not be readily detectable using a particular oligonucleotide probe of the polynucleotide encoding SCSH, and improper or unexpected hybridization to allelic variants, with a locus other than the normal chromosomal locus for the polynucleotide sequence encoding SCSH. The encoded protein may also be "altered," and may contain deletions, insertions, or substitutions of amino acid residues which produce a silent change and result in a functionally equivalent SCSH. Deliberate amino acid substitutions may be made on the basis of similarity in polarity, charge, solubility, hydrophobicity, hydrophilicity, and/or the amphipathic nature of the residues, as long as the biological or immunological activity of SCSH is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments," "immunogenic fragments," or "antigenic fragments" refer to fragments of SCSH which are preferably at least 5 to about 15 amino acids in length, most preferably at least 14 amino acids, and which retain some biological activity or immunological activity of SCSH. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer, a Laboratory Manual*, Cold Spring Harbor Press, Plainview, N.Y., pp.1–5.)

The term "antagonist," as it is used herein, refers to a molecule which, when bound to SCSH, decreases the amount or the duration of the effect of the biological δr immunological activity of SCSH. Antagonists may include proteins, nucleic acids, carbohydrates, antibodies, or any other molecules which decrease the effect of SCSH.

As used herein, the term "antibody" refers to intact molecules as well as to fragments thereof, such as Fab, $F(ab')_2$, and Fv fragments, which are capable of binding the epitopic determinant. Antibodies that bind SCSH polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic SCSH, or of any oligopeptide thereof, to induce a specific immune response in appropriate animals or cells and to bind with specific antibodies.

The terms "complementary" or "complementarity," as used herein, refer to the natural binding of polynucleotides by base pairing. For example, the sequence "5' A-G-T 3'" binds to the complementary sequence "3' T-C-A 5'." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation or an aqueous solution. Compositions comprising polynucleotide sequences encoding SCSH or fragments of SCSH may be employed as hybridization probes. The probes may be stored in freeze-dried form and may be associated with a stabilizing agent such as a carbohydrate. In hybridizations, the probe may be deployed in an aqueous solution containing salts, e.g., NaCl, detergents, e.g., sodium dodecyl sulfate (SDS), and other components, e.g., Denhardt's solution, dry milk, salmon sperm DNA, etc.

"Consensus sequence," as used herein, refers to a nucleic acid sequence which has been resequenced to resolve uncalled bases, extended using XL-PCR kit (The Perkin-Elmer Corp., Norwalk, Conn.) in the 5' and/or the 3' direction, and resequenced, or which has been assembled from the overlapping sequences of more than one Incyte Clone using a computer program for fragment assembly, such as the GELVIEW™ Fragment Assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding SCSH, by Northern analysis is indicative of the presence of nucleic acids encoding SCSH in a sample, and thereby correlates with expression of the transcript from the polynucleotide encoding SCSH.

A "deletion," as the term is used herein, refers to a change in the amino acid or nucleotide sequence that results in the absence of one or more amino acid residues or nucleotides.

The term "derivative," as used herein, refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "similarity," as used herein, refers to a degree of complementarity. There may be partial similarity or complete similarity. The word "identity" may substitute for the word "similarity." A partially complementary sequence that at least partially inhibits an identical sequence from hybridizing to a target nucleic acid is referred to as "substantially similar." The inhibition of hybridization of the completely complementary sequence to the target sequence may be examined using a hybridization assay (Southern or Northern blot, solution hybridization, and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% similarity or identity). In the absence of non-specific binding, the substantially similar sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MEGALIGN program (DNASTAR). The MEGALIGN program can create alignments between two or more sequences according to different methods, e.g., the clustal method. (See, e.g., Higgins, D. G. and P. M. Sharp (1988) Gene 73:237–244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs), as described herein, are linear microchromosomes which may contain DNA sequences of about 6 kb to 10 Mb in size, and which contain all of the elements required for stable mitotic chromosome segregation and maintenance. (See, e.g., Harrington, J. J. et al. (1997) Nat Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, infectious or genetic disease, etc. These conditions can be characterized by expression of various factors, e.g., cytokines, chemokines, and other signaling molecules which may affect cellular and systemic defense systems.

The term "microarray", as used herein, refers to an arrangement of distinct polynucleotides arrayed on a substrate, e.g., paper, nylon or any other type of membrane, filter, chip, glass slide, or any other suitable solid support.

The terms "element" or "array element", as used herein in a microarray context, refer to hybridizable polynucleotides arranged on the surface of a substrate.

The term "modulate," as it appears herein, refers to a change in the activity of SCSH. For example, modulation may cause an increase or a decrease in protein activity, binding characteristics, or any other biological, functional, or immunological properties of SCSH.

The phrases "nucleic acid" or "nucleic acid sequence," as used herein, refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which, when translated, would produce polypeptides retaining some functional characteristic, e.g., antigenicity, or structural domain characteristic, e.g., ATP-binding site, of the full-length polypeptide.

The terms "operably associated" or "operably linked," as used herein, refer to functionally related nucleic acid sequences. A promoter is operably associated or operably linked with a coding sequence if the promoter controls the translation of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimer," "primer," "oligomer," and "probe," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell. (See, e.g., Nielsen, P. E. et al. (1993) Anticancer Drug Des. 8:53–63.)

The term "sample," as used herein, is used in its broadest sense. A biological sample suspected of containing nucleic acids encoding SCSH, or fragments thereof, or SCSH itself, may comprise a bodily fluid; an extract from a cell, chromosome, organelle, or membrane isolated from a cell; a cell; genomic DNA, RNA, or cDNA, in solution or bound to a solid support; a tissue; a tissue print; etc.

As used herein, the terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotides and the claimed polynucleotides. Stringent conditions can be defined by salt concentration, the concentration of organic solvent, e.g., formamide, temperature, and other conditions well known in the art. In particular, stringency can be increased by reducing the concentration of salt, increasing the concentration of formamide, or raising the hybridization temperature.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of SCSH polypeptides, as used herein, refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software (DNASTAR).

The term "variant," when used in the context of a polynucleotide sequence, may encompass a polynucleotide sequence related to SCSH. This definition may also include, for example, "allelic" (as defined above), "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one base. The presence of SNPs may be indicative of, for example, a certain population, a disease state, or a propensity for a disease state.

The Invention

The invention is based on the discovery of new human succinyl-CoA synthetase holoenzyme (SCSH), the polynucleotides encoding SCSH, and the use of these compositions for the diagnosis, treatment, or prevention of neoplastic, reproductive, immunological, vesicle trafficking, and nervous disorders.

Nucleic acids encoding the SCSH-1 of the present invention were first identified in Incyte Clone 2499773 from the adrenal cDNA library (ADRETUT05) using a computer search, e.g., BLAST, for amino acid sequence alignments. A consensus sequence, SEQ ID NO:2, was derived from the following overlapping and/or extended nucleic acid sequences: Incyte Clones 2499773H1 (ADRETUT05), 2659093H1 (LUNGTUT09), 306172H1 (HEARNOT01), 2190667H1 (THYRTUT03), 2158448F6 (BRAINOT09), and 1995417R6 (BRSTTUT03).

Nucleic acids encoding the SCSH-2 of the present invention were first identified in Incyte Clone 3273853 from the prostate cDNA library (PROSBPT06) using a computer search, e.g., BLAST, for amino acid sequence alignments. A consensus sequence, SEQ ID NO:4, was derived from the following overlapping and/or extended nucleic acid sequences: Incyte Clones 3273853H1 and 3273853CT1 (PROSBPT06), and 3046243H1 (HEAANOT01).

In one embodiment, the invention encompasses a polypeptide comprising the amino acid sequence of SEQ ID NO:1, SCSH-1 is 346 amino acids in length and has two potential N-glycosylation sites at residues N232 and N245; two potential casein kinase II phosphorylation sites at residues T103 and S247; two potential protein kinase C phosphorylation sites at residues T64 and T103. In addition, there are ATP-citrate lyase and succinyl-CoA ligase active site signatures from residues M297 to A302. As shown in FIGS. 1A and 1B, SCSH-1 has chemical and structural similarity with pig SCSα subunit (GI 2258465; SEQ ID NO:5). In particular, SCSH-1 and pig SCS α subunit share 89% identity, one potential N-glycosylation site, one potential casein kinase II phosphorylation site, two potential protein kinase C phosphorylation sites, and the succinyl-CoA ligase active site signature. In addition, SCSH and pig SCS α subunit have rather similar isoelectric points, 9.0 and 9.6, respectively. A fragment of SEQ ID NO:2 from about nucleotide 41 to about nucleotide 64 is useful, for example, for designing oligonucleotides or as a hybridization probe. Northern analysis shows the expression of this sequence in various libraries, at least 57% of which are immortalized or cancerous and at least 32% of which involve immune response. Of particular note is the expression of SCSH-1 in reproductive (29%), cardiovascular (15%), gastrointestinal (16%), and nervous tissue (12%).

In another embodiment, the invention encompasses a polypeptide comprising the amino acid sequence of SEQ ID NO:3. SCSH-2 is 432 amino acids in length and has a potential N-glycosylation site at N406; six potential casein kinase II phosphorylation sites at residues T64, T130, S183, T238, S280, and S414; and four potential protein kinase C phosphorylation sites at residues T33, S34, S45, and T130. As shown in FIGS. 2A and 2B, SCSH-2 has chemical and structural similarity with pig SCSβ subunit (GI 164669; SEQ ID NO:6). In particular, SCSH-2 and pig SCS β subunit share 88% identity, six potential casein kinase II phosphorylation sites, and three potential protein kinase C phosphorylation sites. In addition, SCSH-2 and pig SCS β subunit have rather similar isoelectric points, 6.1 and 5.3, respectively. A fragment of SEQ ID NO:4 from about nucleotide 69 to about nucleotide 92 is useful, for example, for designing oligonucleotides or as a hybridization probe. Northern analysis shows the expression of this sequence in various libraries, at least 58% of which are immortalized or cancerous and at least 37% of which involve immune response. Of particular note is the expression of SCSH-2 in reproductive (24%), gastrointestinal (20%), and nervous tissue (15%).

The invention also encompasses SCSH variants. A preferred SCSH variant is one which already exceeds at least about 90%, and more preferably at least about 95%, amino acid sequence identity to the SCSH amino acid sequence, and which contains at least one functional or structural characteristic of SCSH.

The invention also encompasses polynucleotides which encode SCSH. In a particular embodiment, the invention encompasses a polynucleotide sequence comprising the sequence of SEQ ID NO:2 or SEQ ID NO:4, which encode an SCSH.

The invention also encompasses a variant of a polynucleotide sequence encoding SCSH. In particular, such a variant polynucleotide sequence will have at least about 85% identity to the polynucleotide sequence encoding SCSH.

It will be appreciated by those skilled in the art that as a result of the degeneracy of the genetic code, a multitude of polynucleotide sequences encoding SCSH, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring SCSH, and all such variations are to be considered as being specifically disclosed.

Although nucleotide sequences which encode SCSH and its variants are preferably capable of hybridizing to the nucleotide sequence of the naturally occurring SCSH under appropriately selected conditions of stringency, it may be advantageous to produce nucleotide sequences encoding SCSH possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding SCSH and its derivatives without altering the encoded amino acid sequences include the production of RNA transcripts having more desirable properties, such as a greater half-life, than transcripts produced from the naturally occurring sequence.

The invention also encompasses production of DNA sequences which encode SCSH and SCSH derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding SCSH or any fragment thereof.

Also encompassed by the invention are polynucleotide sequences that are capable of hybridizing to the claimed polynucleotide sequences, and, in particular, to those shown in SEQ ID NO:2, or a fragment of SEQ ID NO:2, SEQ ID NO:4, a fragment of SEQ ID NO:2, or a fragment of SEQ ID NO:4, under various conditions of stringency. (See, e.g., Wahl, G. M. and S. L. Berger (1987) Methods Enzymol. 152:399–407; Kimmel, A. R. (1987) Methods Enzymol. 152:507–511.) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Stringent hybridization can be obtained in the absence of organic solvent, e.g., formamide, and high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 68°–72° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

Methods for DNA sequencing and analysis are well known in the art. The methods may employ such enzymes as the Klenow fragment of DNA polymerase I, SEQUENASE® (Amersham Pharmacia Biotech Ltd., Uppsala, Sweden), Taq polymerase (The Perkin-Elmer Corp., Norwalk, Conn.), thermostable T7polymerase (Amersham Pharmacia Biotech), or combinations of polymerases and proofreading exonucleases, such as those found in the ELONGASE amplification system (Life Technologies, Inc., Rockville, Md.). Preferably, sequence preparation is automated with machines, e.g., the ABI CATALYST 800 (Perkin-Elmer) or MICROLAB® (Hamilton Co., Reno, Nev.) systems, in combination with thermal cyclers. Sequencing can also be automated, such as by ABI PRISM 373 or 377 systems (Perkin-Elmer) or the MEGABACE 1000 capillary electrophoresis system (Molecular Dynamics, Inc., Sunnyvale, Calif.). Sequences can be analyzed using computer programs and algorithms well known in the art. (See, e.g., Ausubel, F. M. et al. (1997) supra, unit 7.7; and Meyers, R. A. (1995) *Molecular Biology and Biotechnology*, Wiley VCH, Inc, New York, N.Y.)

The nucleic acid sequences encoding SCSH may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111–119.) In this method, multiple restriction enzyme digestions and ligations may be used to insert an engineered double-stranded sequence into a region of unknown sequence before performing PCR.

Other methods which may be used to retrieve unknown sequences are known in the art. (See, e.g., Parker, J. D. et al. (1991) Nucleic Acids Res. 19:3055–306.) Additionally, one may use PCR, nested primers, and PromoterFinder libraries (Clontech, Palo Alto, Calif.) to walk genomic DNA. This procedure avoids the need to screen libraries and is useful in finding intron/exon junctions. For all PCR-based methods, primers may be designed using commercially available software, such as OLIGO 4.06 Primer Analysis software (National Biosciences Inc., Plymouth, Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., GENOTYPER and SEQUENCE NAVIGATOR, Perkin Elmer), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode SCSH may be cloned in recombinant DNA molecules that direct expression of SCSH, or fragments or functional equivalents thereof, in appropriate host cells. Due to the inherent degeneracy of the genetic code, other DNA sequences which encode substantially the same or a functionally equivalent amino acid sequence may be produced and used to express SCSH.

The nucleotide sequences of the present invention can be engineered using methods generally known in the art in order to alter SCSH-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding SCSH may be synthesized, in whole or in part, using chemical methods well known in the art. (See, e.g., Caruthers, M. H. et al. (1980) Nucl. Acids Res. Symp. Ser. 215–223, and Horn, T. et al. (1980) Nucl. Acids Res. Symp. Ser. 225–232.) Alternatively, SCSH itself or a fragment thereof may be synthesized using chemical methods. For example, peptide synthesis can be performed using various solid-phase techniques. (See, e.g., Roberge, J. Y. et al. (1995) Science 269:202–204.) Automated synthesis may be achieved using the ABI 431 A Peptide Synthesizer (Perkin-Elmer). Additionally, the amino acid sequence of SCSH, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1984) *Proteins, Structures and Molecular Properties*, W H Freeman and Co., New York, N.Y.)

In order to express a biologically active SCSH, the nucleotide sequences encoding SCSH or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding SCSH. Such elements may vary in their strength and specificity. Specific initiation signals may also be used to achieve more efficient translation of sequences encoding SCSH. Such signals include the ATG initiation codon and adjacent sequences, e.g. the Kozak sequence. In cases where sequences encoding SCSH and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125–162.)

Methods which are well known to those skilled in the art may be used to construct expression vectors containing sequences encoding SCSH and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual*, Cold Spring Harbor Press, Plainview, N.Y., ch. 4, 8, and 16–17; and Ausubel, F. M. et al. (1995, and periodic supplements) *Current Protocols in Molecular Biology*, John Wiley & Sons, New York, N.Y., ch. 9, 13, and 16.)

A variety of expression vector/host systems may be utilized to contain and express sequences encoding SCSH. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

In bacterial systems, a number of cloning and expression vectors may be selected depending upon the use intended for polynucleotide sequences encoding SCSH. For example, routine cloning, subcloning, and propagation of polynucleotide sequences encoding SCSH can be achieved using a multifunctional *E. coli* vector such as BLUESCRIPT PLASMID (Stratagene, La Jolla, Calif.) or PSPORT1 plasmid (Life Technologies). Ligation of sequences encoding SCSH into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503–5509.) When large quantities of SCSH are needed, e.g. for the production of antibodies, vectors which direct high level expression of SCSH may be used. For example, vectors containing the strong, inducible T5 or T7 bacteriophage promoter may be used.

Yeast expression systems may be used for production of SCSH. A number of vectors containing constitutive or inducible promoters, such as alpha factor, alcohol oxidase, and PGH, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, supra; and Grant et al. (1987) Methods Enzymol. 153:516–54; Scorer, C. A. et al. (1994) Bio/Technology 12:181–184.)

Plant systems may also be used for expression of SCSH. Transcription of sequences encoding SCSH may be driven viral promoters, e.g., the 35S and 19S promoters of CaMV used alone or in combination with the omega leader sequence from TMV. (Takamatsu, N. (1987) EMBO J. 6:307–311.) Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. (See, e.g., Hobbs, S. or Murry, L. E. in *McGraw Hill Yearbook of Science and Technology* (1992) McGraw Hill, New York, N.Y.; pp. 191–196.)

In mammalian cells, a number of viral-based expression systems may be utilized. In cases where an adenovirus is used as an expression vector, sequences encoding SCSH may be ligated into an adenovirus transcription/translation complex consisting of the late promoter and tripartite leader sequence. Insertion in a non-essential E1 or E3 region of the viral genome may be used to obtain infective virus which expresses SCSH in host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes.

For long term production of recombinant proteins in mammalian systems, stable expression of SCSH in cell lines is preferred. For example, sequences encoding SCSH can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk$^-$ or apr$^-$ cells, respectively. (See, e.g., Wigler, M. et al. (1977) Cell 11:223–232; and Lowy, I. et al. (1980) Cell 22:817–823.) Also, antimetabolite, antibiotic, or herbicide resistance can be used as the basis for selection. For example, dhfr confers resistance to methotrexate; neo confers resistance to the aminoglycosides neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al (1981) J. Mol. Biol. 150:1–14; and Murry, supra.) Additional selectable genes have been described, e.g., trpB and hisD, which alter cellular requirements for metabolites. (See, e.g., Hartman, S. C. and R. C. Mulligan (1988) Proc. Natl. Acad. Sci. 85:8047–8051.) Visible markers, e.g., anthocyanins, green fluorescent proteins (GFP; Clontech), β glucuronidase and its substrate β-D-glucuronoside, or luciferase and its substrate luciferin may be used. These markers can be used not only to identify transformants, but also to quantify the amount of transient or stable protein expression attributable to a specific vector system. (See, e.g., Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding SCSH is inserted within a marker gene sequence, transformed cells containing sequences encoding SCSH can be identified by the absence of marker gene function. Alternatively, a marker gene can be placed in tandem with a sequence encoding SCSH under the control of a single promoter. Expression of the marker gene in response to induction or selection usually indicates expression of the tandem gene as well.

In general, host cells that contain the nucleic acid sequence encoding SCSH and that express SCSH may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of SCSH using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on SCSH is preferred, but a competitive binding assay may be employed. These and other assays are well known in the art. (See, e.g., Hampton, R. et al. (1990) *Serological Methods, a Laboratory Manual*, APS Press, St Paul, Minn., Section IV; Coligan, J. E. et al. (1997 and periodic supplements) *Current Protocols in Immunology*, Greene Pub. Associates and Wiley-Interscience, New York, N.Y.; and Maddox, D. E. et al. (1983) J. Exp. Med. 158:1211–1216.)

A wide variety of labels and conjugation techniques are known by those skilled in the art and may be used in various nucleic acid and amino acid assays. Means for producing labeled hybridization or PCR probes for detecting sequences related to polynucleotides encoding SCSH include oligolabeling, nick translation, end-labeling, or PCR amplification using a labeled nucleotide. Alternatively, the sequences encoding SCSH, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by (Amersham Pharmacia Biotech, Promega (Madison, Wis.) and US Biochemical). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding SCSH may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode SCSH may be designed to contain signal sequences which direct secretion of SCSH through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and W138), are available from the American Type Culture Collection (ATCC, Bethesda, Md.) and may be chosen to ensure the correct modification and processing of the foreign protein.

In another embodiment of the invention, natural, modified, or recombinant nucleic acid sequences encoding SCSH may be ligated to a heterologous sequence resulting in translation of a fusion protein in any of the aforementioned host systems. For example, a chimeric SCSH protein containing a heterologous moiety that can be recognized by a commercially available antibody may facilitate the screening of peptide libraries for inhibitors of SCSH activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the SCSH encoding sequence and the heterologous protein sequence, so that SCSH may be cleaved away from the heterologous moiety following purification. Methods for fusion protein expression and purification are discussed in Ausubel, F. M. et al. (1995; supra, ch 10). A variety of commercially available kits may also be used to facilitate expression and purification of fusion proteins.

In a further embodiment of the invention, synthesis of radiolabeled SCSH may be achieved in vitro using the TNT rabbit reticulocyte lysate or wheat germ extract systems (Promega). These systems couple transcription and translation of protein-coding sequences operably associated with the T7, T3, or SP6 promoters. Translation takes place in the presence of a radiolabeled amino acid precursor, preferably $^{35}$S-methionine.

Fragments of SCSH may be produced not only by recombinant production, but also by direct peptide synthesis using solid-phase techniques. (See, e.g., Creighton, supra pp. 55–60.) Protein synthesis may be performed by manual techniques or by automation. Automated synthesis may be achieved, for example, using the Applied Biosystems 431A Peptide Synthesizer (Perkin-Elmer Corp.). Various fragments of SCSH may be synthesized separately and then combined to produce the full length molecule.

Therapeutics

Chemical and structural similarity, e.g., in the context of sequences and motifs, exists between SCSH-1 and pig SCS α subunit (GI 2258465). In addition, SCSH-1 is expressed in neoplastic, immunological, reproductive, cardiovascular, gastrointestinal, and nervous tissue. Therefore, SCSH-1 appears to play a role in neoplastic, reproductive, immunological, vesicle trafficking, and nervous disorders.

Chemical and structural similarity, e.g., in the context of sequences and motifs, exists between SCSH-2 and pig SCS β subunit (GI 164669). In addition, SCSH-2 is expressed in neoplastic, immunological, reproductive, gastrointestinal, and nervous tissue. Therefore, SCSH-2 appears to play a role in neoplastic, reproductive, immunological, vesicle trafficking, and nervous disorders.

Therefore, in one embodiment, an antagonist of SCSH may be administered to a subject to treat or prevent a neoplastic disorder. Such a neoplastic disorder may include, but is not limited to, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds SCSH may be used directly as an antagonist or indirectly as a targeting or delivery mechanism for bringing a pharmaceutical agent to cells or tissue which express SCSH.

In an additional embodiment, a vector expressing the complement of the polynucleotide encoding SCSH may be administered to a subject to treat or prevent a neoplastic disorder including, but not limited to, those described above.

In a further embodiment, an antagonist of SCSH may be administered to a subject to treat or prevent a reproductive disorder. Such a reproductive disorder may include, but is not limited to, disorders of prolactin production; infertility, including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, uterine fibroids, autoimmune disorders, ectopic pregnancies, and teratogenesis; cancer of the breast, fibrocystic breast disease, and galactorrhea; disruptions of spermatogenesis, abnormal sperm physiology, cancer of the testis, cancer of the prostate, benign prostatic hyperplasia, prostatitis, Peyronie's disease, carcinoma of the male breast, and gynecomastia. In one aspect, an antibody which specifically binds SCSH may be used directly as an antagonist or indirectly as a targeting or delivery mechanism for bringing a pharmaceutical agent to cells or tissue which express SCSH.

In an additional embodiment, a vector expressing the complement of the polynucleotide encoding SCSH may be administered to a subject to treat or prevent a reproductive disorder including, but not limited to, those described above.

In a further embodiment, an antagonist of SCSH may be administered to a subject to treat or prevent an immunological disorder. Such an immunological disorder may include, but is not limited to, acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma. In one aspect, an antibody which specifically binds SCSH may be used directly as an antagonist or indirectly as a targeting or delivery mechanism for bringing a pharmaceutical agent to cells or tissue which express SCSH.

In an additional embodiment, a vector expressing the complement of the polynucleotide encoding SCSH may be administered to a subject to treat or prevent an immunological disorder including, but not limited to, those described above.

In a further embodiment, an antagonist of SCSH may be administered to a subject to treat or prevent a vesicle trafficking disorder. Such a vesicle trafficking disorder may include, but is not limited to, cystic fibrosis, glucose-galactose malabsorption syndrome, hypercholesterolemia, diabetes mellitus, diabetes insipidus, hyper- and hypoglycemia, Grave's disease, goiter, Cushing's disease, and Addison's disease; gastrointestinal disorders including ulcerative colitis, gastric and duodenal ulcers; other conditions associated with abnormal vesicle trafficking, including acquired immunodeficiency syndrome (AIDS); allergies including hay fever, asthma, and urticaria (hives); autoimmune hemolytic anemia; proliferative glomerulonephritis; inflammatory bowel disease; multiple sclerosis; myasthenia gravis; rheumatoid and osteoarthritis; scleroderma;

Chediak-Higashi and Sjogren's syndromes; systemic lupus erythematosus; toxic shock syndrome; traumatic tissue damage; and viral, bacterial, fungal, helminthic, and protozoal infections. In one aspect, an antibody which specifically binds SCSH may be used directly as an antagonist or indirectly as a targeting or delivery mechanism for bringing a pharmaceutical agent to cells or tissue which express SCSH.

In an additional embodiment, a vector expressing the complement of the polynucleotide encoding SCSH may be administered to a subject to treat or prevent a vesicle trafficking disorder including, but not limited to, those described above.

In a further embodiment, an antagonist of SCSH may be administered to a subject to treat or prevent a nervous disorder. Such a nervous disorder may include, but is not limited to, epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease; prion diseases including kuru, Creutzfeldt-Jakob disease, and Gerstmann-Straussler-Scheinker syndrome; fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis; inherited, metabolic, endocrine, and toxic myopathies; myasthenia gravis, periodic paralysis; mental disorders including mood, anxiety, and schizophrenic disorders; akathesia, amnesia, catatonia, diabetic neuropathy, tardive dyskinesia, dystonias, paranoid psychoses, postherpetic neuralgia, and Tourette's disorder. In one aspect, an antibody which specifically binds SCSH may be used directly as an antagonist or indirectly as a targeting or delivery mechanism for bringing a pharmaceutical agent to cells or tissue which express SCSH.

In an additional embodiment, a vector expressing the complement of the polynucleotide encoding SCSH may be administered to a subject to treat or prevent a nervous disorder including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of SCSH may be produced using methods which are generally known in the art. In particular, purified SCSH may be used to produce antibodies or to screen libraries of pharmaceutical agents to identify those which specifically bind SCSH. Antibodies to SCSH may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of polyclonal antibodies, various hosts including goats, rabbits, rats, mice, humans, and others may be immunized by injection with SCSH or with any fragment or oligopeptide thereof which has immunogenic properties. Rats and mice are preferred hosts for downstream applications involving monoclonal antibody production. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable. (For review of methods for antibody production and analysis, see, e.g., Harlow, E. and Lane, D. (1988) *Antibodies: A Laboratory Manual*, Cold Spring Harbor Laboratory, Cold Spring Harbor, N.Y.)

It is preferred that the oligopeptides, peptides, or fragments used to induce antibodies to SCSH have an amino acid sequence consisting of at least about 5 amino acids, and, more preferably, of at least about 14 amino acids. It is also preferable that these oligopeptides, peptides, or fragments are identical to a portion of the amino acid sequence of the natural protein and contain the entire amino acid sequence of a small, naturally occurring molecule. Short stretches of SCSH amino acids may be fused with those of another protein, such as KLH, and antibodies to the chimeric molecule may be produced.

Monoclonal antibodies to SCSH may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce SCSH-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86:3833–3837; and Winter, G. et al. (1991) Nature 349:293–299.)

Antibody fragments which contain specific binding sites for SCSH may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity and minimal cross-reactivity. Numerous protocols for competitive binding or immunoradiometric assays using either polyclonal or monoclonal antibodies with established specificities are well known in the art. Such immunoassays typically involve the measurement of complex formation between SCSH and its specific antibody. A two-site, monoclonal-based immunoassay utilizing monoclonal antibodies reactive to two non-interfering SCSH epitopes is preferred, but a competitive binding assay may also be employed. (Maddox, supra.)

Various methods such as Scatchard analysis in conjunction with radioimmunoassay techniques may be used to assess the affinity of antibodies for SCSH. Affinity is expressed as an association constant, $K_a$, which is defined as the molar concentration of SCSH-antibody complex divided by the molar concentrations of free antigen and free antibody under equilibrium conditions. The $K_a$ determined for a preparation of polyclonal antibodies, which are heterogeneous in their affinities for multiple SCSH epitopes, represents the average affinity, or avidity, of the antibodies for SCSH. The $K_a$ determined for a preparation of monoclonal antibodies, which are monospecific for a particular SCSH epitope, represents a true measure of affinity. High-affinity antibody preparations with $K_a$ ranging from about $10^9$ to $10^{12}$ L/mole are preferred for use in immunoassays in which the SCSH-antibody complex must withstand rigorous manipulations. Low-affinity antibody preparations with $K_a$ ranging from about $10^6$ to $10^7$ L/mole are preferred for use in immunopurification and similar procedures which ultimately require dissociation of SCSH, preferably in active form, from the antibody. (Catty, D. (1988) *Antibodies, Volume I: A Practical Approach*, IRL Press, Washington, D.C.; and Liddell, J. E. and Cryer, A. (1991) *A Practical Guide to Monoclonal Antibodies*, John Wiley & Sons, New York, N.Y.)

The titre and avidity of polyclonal antibody preparations may be further evaluated to determine the quality and suitability of such preparations for certain downstream applications. For example, a polyclonal antibody preparation containing at least 1–2 mg specific antibody/ml, preferably 5–10 mg specific antibody/ml, is preferred for use in procedures requiring precipitation of SCSH-antibody complexes. Procedures for evaluating antibody specificity, titer, and avidity, and guidelines for antibody quality and usage in various applications, are generally available. (See, e.g., Catty, supra, and Coligan et al. supra.)

In another embodiment of the invention, the polynucleotides encoding SCSH, or any fragment or complement thereof, may be used for therapeutic purposes. In one aspect, the complement of the polynucleotide encoding SCSH may be used in situations in which it would be desirable to block the transcription of the mRNA. In particular, cells may be transformed with sequences complementary to polynucleotides encoding SCSH. Thus, complementary molecules or fragments may be used to modulate SCSH activity, or to achieve regulation of gene function. Such technology is now well known in the art, and sense or antisense oligonucleotides or larger fragments can be designed from various locations along the coding or control regions of sequences encoding SCSH.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors to express nucleic acid sequences complementary to the polynucleotides encoding SCSH. (See, e.g., Sambrook, supra; and Ausubel, supra.)

Genes encoding SCSH can be turned off by transforming a cell or tissue with expression vectors which express high levels of a polynucleotide, or fragment thereof, encoding SCSH. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding SCSH. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing Co., Mt. Kisco, N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding SCSH.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding SCSH. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of SCSH, antibodies to SCSH, and mimetics, agonists, antagonists, or inhibitors of SCSH. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of SCSH, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example SCSH or fragments thereof, antibodies of SCSH, and agonists, antagonists or inhibitors of SCSH, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of therapeutic to toxic effects is the therapeutic index, and it can be expressed as the $ED_{50}/LD_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 µg to 100,000 µg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind SCSH may be used for the diagnosis of disorders characterized by expression of SCSH, or in assays to monitor patients being treated with SCSH or agonists, antagonists, or inhibitors of SCSH. Antibodies useful for diagnostic purposes may be prepared in the same manner as described above for therapeutics. Diagnostic assays for SCSH include methods which utilize the antibody and a label to detect SCSH in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring SCSH, including ELISAs, RIAs, and FACS, are known in the art and provide a basis for diagnosing altered or abnormal levels of SCSH expression. Normal or standard values for SCSH expression are established by combining body fluids or cell extracts taken from normal mammalian subjects, preferably human, with antibody to SCSH under conditions suitable for complex formation The amount of standard complex formation may be quantitated by various methods, preferably by photometric means. Quantities of SCSH expressed in subject, control, and disease samples from biopsied tissues are compared with the standard values. Deviation between standard and subject values establishes the parameters for diagnosing disease.

In another embodiment of the invention, the polynucleotides encoding SCSH may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of SCSH may be correlated with disease. The diagnostic assay may be used to determine absence, presence, and excess expression of SCSH, and to monitor regulation of SCSH levels during therapeutic intervention.

In one aspect, hybridization with PCR probes which are capable of detecting polynucleotide sequences, including genomic sequences, encoding SCSH or closely related molecules may be used to identify nucleic acid sequences which encode SCSH. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding SCSH, allelic variants, or related sequences.

Probes may also be used for the detection of related sequences, and should preferably have at least 50% sequence identity to any of the SCSH encoding sequences. The hybridization probes of the subject invention may be DNA or RNA and may be derived from the sequences of SEQ ID NO:2, SEQ ID NO:4, or from genomic sequences including promoters, enhancers, and introns of the SCSH gene.

Means for producing specific hybridization probes for DNAs encoding SCSH include the cloning of polynucleotide sequences encoding SCSH or SCSH derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding SCSH may be used for the diagnosis of a disorder associated with expression of SCSH. Examples of such a disorder include, but are not limited to, a neoplastic disorder, such as, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; a reproductive disorder, such as, disorders of prolactin production; infertility, including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, uterine fibroids, autoimmune disorders, ectopic pregnancies, and teratogenesis; cancer of the breast, fibrocystic breast disease, and galactorrhea; disruptions of spermatogenesis, abnormal sperm physiology, cancer of the testis, cancer of the prostate, benign prostatic hyperplasia, prostatitis, Peyronie's disease, carcinoma of the male breast, and gynecomastia; an immunological disorder, such as, acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; a vesicle trafficking disorder, such as, cystic fibrosis, glucose-galactose malabsorption syndrome, hypercholesterolemia, diabetes mellitus, diabetes insipidus, hyper- and hypoglycemia, Grave's disease, goiter, Cushing's disease, and Addison's disease; gastrointestinal disorders including ulcerative colitis, gastric and duodenal ulcers; other conditions associated with abnormal vesicle trafficking, including acquired immunodeficiency syndrome (AIDS); allergies including hay fever, asthma, and urticaria (hives); autoimmune hemolytic anemia; proliferative glomerulonephritis; inflammatory bowel disease; multiple sclerosis; myasthenia gravis; rheumatoid and osteoarthritis; scleroderma; Chediak-Higashi and Sjogren's syndromes; systemic lupus erythematosus; toxic shock syndrome; traumatic tissue damage; and viral, bacterial, fungal, helminthic, and protozoal infections; and a nervous disorder, such as, epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease; prion diseases including kuru, Creutzfeldt-Jakob disease, and Gerstmann-Straussler-Scheinker syndrome; fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis; inherited, metabolic, endocrine, and toxic myopathies; myasthenia gravis, periodic paralysis; mental disorders including mood, anxiety, and schizophrenic disorders; akathesia, amnesia, catatonia, diabetic neuropathy, tardive dyskinesia, dystonias, paranoid psychoses, postherpetic neuralgia, and Tourette's disorder. The polynucleotide sequences encoding SCSH may be used in Southern or Northern analysis, dot blot, or other membrane-based technologies; in PCR technologies; in dipstick, pin, and ELISA assays; and in microarrays utilizing fluids or tissues from patients to detect altered SCSH expression. Such qualitative or quantitative methods are well known in the art.

In a particular aspect, the nucleotide sequences encoding SCSH may be useful in assays that detect the presence of associated disorders, particularly those mentioned above. The nucleotide sequences encoding SCSH may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding SCSH in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of SCSH, a normal or standard profile for expression is established. This may be accomplished by combining body fluids or cell extracts taken from normal subjects, either animal or human, with a sequence, or a fragment thereof, encoding SCSH, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding SCSH may involve the use of PCR. These oligomers may be chemically synthesized, generated enzymatically, or produced in vitro. Oligomers will preferably contain a fragment of a polynucleotide encoding SCSH, or a fragment of a polynucleotide complementary to the polynucleotide encoding SCSH, and will be employed under optimized conditions for identification of a specific gene or condition. Oligomers may also be employed under less stringent conditions for detection or quantitation of closely related DNA or RNA sequences.

Methods which may also be used to quantitate the expression of SCSH include radiolabeling or biotinylating nucleotides, coamplification of a control nucleic acid, and interpolating results from standard curves. (See, e.g., Melby, P. C. et al. (1993) J. Immunol. Methods 159:235–244; and Duplaa, C. et al. (1993) Anal. Biochem. 229–236.) The speed of quantitation of multiple samples may be accelerated by running the assay in an ELISA format where the oligomer of interest is presented in various dilutions and a spectrophotometric or calorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding SCSH may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome libraries. (See, e.g., Price, C. M. (1993) Blood Rev. 7:127–134; Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, supra pp. 965–968). Examples of genetic map data can be found in various scientific journals or at the Online Mendelian Inheritance in Man (OMIM) site. Correlation between the location of the gene encoding SCSH on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., ataxia-telangiectasia to 11q22–23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, SCSH, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between SCSH and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate, such as plastic pins or some other surface. The test compounds are reacted with SCSH, or fragments thereof, and washed. Bound SCSH is then detected by methods well known in the art. Purified SCSH can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding SCSH specifically compete with a test compound for binding SCSH. In this manner, antibodies can be used to detect the presence of any peptide which shares one or more antigenic determinants with SCSH.

In additional embodiments, the nucleotide sequences which encode SCSH may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. Construction of cDNA Libraries

ADRETUT05

The ADRETUT05 library was constructed using RNA isolated from adrenal tumor tissue removed from a 52-year-old Caucasian female during a unilateral adrenalectomy. Pathology indicated a pheochromocytoma.

PROSBPT06

The PROSBPT06 library was constructed using RNA isolated from diseased prostate tissue removed from a 66-year-old Caucasian male during a radical prostatectomy and lymph node excision. Pathology indicated adenofibromatous hyperplasia. Pathology for the associated tumor tissue indicated grade 2 (of 4) adenocarcinoma, Gleason grade 3+3. The patient presented with elevated prostate specific antigen (PSA), proteinuria, decreased renal function, and urinary frequency. Family history included benign hypertension, cerebrovascular disease, and colon cancer.

For both libraries, the tissue was homogenized and lysed in phenol or a suitable mixture of denaturants such as TRIZOL reagent (Life Technologies), a monophasic solution of phenol and guanidine isothiocyanate, and the lysate was extracted with chloroform (1:5 v/v). RNA was precipitated from lysates with either isopropanol or sodium acetate and ethanol. Alternatively, RNA was purified from lysates by preparative agarose gel electrophoresis and recovered from Whatman P81 paper (Whatman, Lexington, Mass.). Phenol extraction and precipitation of RNA were repeated as necessary to increase RNA purity, and RNA was maintained in RNase-free solutions. In some cases, RNA was treated with DNase. For most libraries, poly(A+) RNA was isolated using oligo d(T)-coupled paramagnetic particles (Promega) resin, or the OLIGOTEX kit (QIAGEN Inc, Chatsworth, Calif.). Alternatively, RNA was isolated directly from tissue lysates using the RNA Isolation kit (Stratagene) or the PolyA Quick kit (Ambion, Austin, Tex.).

RNA was used for cDNA synthesis and construction of the cDNA libraries according to procedures recommended in the UNIZAP vector (Stratagene) or SUPERSCRIPT plasmid system (Life Technologies), both of which are based on methods well known in the art (Ausubel, (1997) supra, units 5.1–6.6). Alternatively, cDNA libraries were constructed by Stratagene using RNA provided by Incyte. Reverse transcription was initiated using oligo d(T) or random primers. Synthetic oligonucleotide adapters were ligated to double stranded cDNA, and cDNA was digested with an appropriate restriction enzyme(s). For most libraries, cDNA was size-selected (300–1000 bp) using Sephacryl S1000 or SEPHAROSE CL2B or CL4B column chromatography (Amersham Pharmacia Biotech) or preparative agarose gel electrophoresis. cDNAs were ligated into compatible restriction enzyme sites of the polylinker of pINCY (Incyte Pharmaceuticals Inc, Palo Alto, Calif.). Recombinant plasmids were transformed into competent E. coli cells, e.g., XL1-BLUE, XL1-BLUEMRF, or SOLR (Stratagene) or DH5α, DH10B, or ELECTROMAX DH10B (Life Technologies).

II. Isolation of cDNA Clones

Plasmids were recovered from host cells by cell lysis. Plasmids were purified using the MAGIC MINIPREPS DNA purification system (Promega), Miniprep kit (Advanced Genetic Technologies Corporation, Gaithersburg, Md.); QIAWELL-8 PLASMID QIAWELL PLUS DNA, or QIAWELL ULTRA DNA purification systems; or REAL Prep 96 plasmid kit (QIAGEN Inc) using the recommended protocol. Following precipitation, plasmids were resuspended in 0.1 ml of distilled water and stored, with or without lyophilization, at 4° C.

Alternatively, plasmid DNA was amplified from host cell lysates using direct link PCR (Rao, V. B. (1994) Anal. Biochem. 216:1–14) in a high-throughput format. Host cell lysis and thermal cycling steps were carried out in a single reaction mixture. Samples were processed and stored in 384-well plates (Genetix Ltd, Christchurch UK) and concentration of amplified plasmid DNA was quantified fluorometrically using Pico Green Dye (Molecular Probes, Eugene Oreg.) and a Fluoroscan II fluorescence scanner (Labsystems Oy, Helsinki, Finland).

III. Similarity Searching of cDNA Clones and Their Deduced Proteins

The cDNAs were prepared for sequencing using either an ABI Catalyst 800 (Perkin Elmer) or a Hamilton Micro Lab 2200 (Hamilton, Reno, Nev.) in combination with Peltier Thermal Cyclers (PTC200; MJ Research, Watertown Mass.). The cDNAs were sequenced on the ABI 373 or 377 DNA Sequencing systems (Perkin Elmer) by the method of Sanger, F and A. R. Coulson (1975; J. Mol. Biol. 94:441–448) using standard ABI protocols, base calling software, and kits. Alternatively, cDNAs were sequenced using solutions and dyes from Amersham Pharmacia Biotech. Reading frame was determined using standard methods (Ausubel, (1997) supra).

The full length nucleotide and amino acid sequences disclosed in the Sequence Listing were queried against databases such as GenBank primate (pri), rodent (rod), mammalian (mamp), vertebrate (vrtp), and eukaryote (eukp) databases, SwissProt, BLOCKS, and other databases which contain previously identified and annotated motifs and sequences. Algorithms such as Smith Waterman which deal with primary sequence patterns and secondary structure gap penalties (Smith, T. et al. (1992) Protein Engineering 5:35–51) and programs and algorithms such as BLAST (Basic Local Alignment Search Tool; Altschul, S. F. (1993) J. Mol. Evol 36:290–300; and Altschul et al. (1990) J. Mol. Biol. 215:403–410), and HMM (Hidden Markov Models; Eddy, S. R. (1996) Cur. Opin. Str. Biol. 6:361–365; and Sonnhammer, E. L. L. et al. (1997) Proteins 28:405–420) were used to assemble and analyze nucleotide and amino acid sequences. The databases, programs, algorithms, methods and tools are available, well known in the art, and described in Ausubel with (1997; supra, unit 7.7), in Meyers, supra, pp 856–853), in documentation provided with software (Genetics Computer Group (GCG), Madison Wis.), and on the world wide web (www). Two comprehensive websites which list, describe, and/or link many of the databases and tools are: 1) the www resource in practical sequence analysis (http://genome.wustl.edu/), and 2) the bibliography of computational gene recognition (http://linkage.rockefeller.edu/wli/gene/programs.html). For example, the first website links PFAM as a database (http://genome.wustl.edu/Pfam/) and as an HMM search tool (http://genome.wustl.edu/eddy/cgibin/hmm_page.cgi).

Table 1 summarizes the databases and tools used herein. The first column of Table 1 shows the tool, program, or algorithm; the second column, the database; the third column, a brief description; and the fourth column (where applicable), scores for determining the strength of a match between two sequences (the higher the value, the more homologous).

IV. Northern Analysis

Northern analysis is a laboratory technique used to detect the presence of a transcript and involves the hybridization of a labeled nucleotide probe to a substrate on which mRNAs from a particular cell type or tissue have been bound (Sambrook, (1995) supra, ch. 7).

Analogous computer techniques can be used to perform an electronic northern analysis. One of these techniques used BLAST to search for identical or related molecules in nucleotide databases such as GenBank or LIFESEQ database (Incyte Pharmaceuticals). This analysis was faster than multiple membrane-based hybridizations, and the sensitivity of the computer search was modified to determine the specificity of any particular match.

TABLE I

| Program/algorithm | Databases | Description | Useful Parameters |
|---|---|---|---|
| ESTs | | | |
| Smith Waterman | GenBank | Local alignment algorithm for homology searching | min length = 49 nt<br><12% uncalled bases |
| FASTA | GenBank | Fast nucleotide sequence database searching program for UNIX, VMS | |
| BLAST | GenBank | Ultra-fast database searching program for UNIX, VMS C source | Log likelihood for exact matches is $\sim 10^{-25}$ and for homologs $> 10^{-8}$ |
| Full Length | | | |
| Phred | | Reads trace data from sequencing runs, makes base calls for assembly of cDNA sequences, produces quality scores | |
| Phrap | | Quality-score based assembly program for shotgun sequences | match > 56<br>score > 120 |
| CONSED | | Graphical tool for editing Phrap contigs | |
| GCG Assembly, Motifs, Profilescan, | GenBank PROSITE | Wisconsing Package Programs for the assembly, editing, and characterization of nucleotide sequences | |
| Spscan | | Examines proteins for secretory, signal sequences | >7 strong,<br>4.5–7 suggestive |
| GENEMARK | | Statistical analysis of nucleotide sequences to identify open reading frame | |
| BLAST | GenBank SwissProt | Ultra-fast database searching program for UNIX, VMS C source | score > 100, P < 1e-5 |
| FASTX | GenBank SwissProt | Fast amino acid sequence database searching program for UNIX, VMS | log likelihood > 17 |
| BLIMPS | BLOCKS PRINTS | Weighted matrix analysis for prediction of protein family | >1300 strong,<br>1000–1300 suggestive,<br>P < 1e-3 |
| PFAM | PROSITE | Analyses sequences 3–60 amino acids long which correspond to highly conserved regions of a protein family | Score > 11 strong,<br>8–10 suggestive |
| HMM | | Probabilistic approaches and modeling of the primary structure of protein families | Score > 11 strong,<br>8–10 suggestive |
| McDNAsis Pro | | Software for sequence analysis | |
| LASERGENE | | Software programs (EditSeq, MegAlign, PrimerSelect, Protean, SeqMan, etc.) for sequence analysis | |

The basis of the search is the product score, which is defined as:

$$\frac{\% \text{ sequence identity} \times \% \text{ maximum BLAST score}}{100}$$

The product score compares the degree of similarity between two sequences and the length of the sequence match. For example, with a product score of 40, the match will be exact within a 1% to 2% error, and, with a product score of 70, the match will be exact. Similar molecules are identified by selecting those which show product scores between 15 and 40, although lower scores may be used to identify related molecules.

The results of electronic Northern analysis were reported in The Invention as the compilation of tissues and disease categories in which the transcript encoding SCSH occurred. Abundance, the number of times a particular transcript was represented in a cDNA library, and percent abundance, abundance divided by the total number of sequences examined in the cDNA library, are compiled into two broader categories. The two categories are tissue distribution and disease. Tissue distribution includes reproductive, cardiovascular, gastrointestinal, nervous, etc., and disease includes cancer, immune, fetal, developmental, etc.

V. Extension of SCSH Encoding Polynucleotides

The nucleic acid sequences of Incyte Clones 2499773 and 3273853 were used to design oligonucleotide primers for extending partial nucleotide sequences to full length. For each nucleic acid sequence, one primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO 4.06 (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (Life Technologies) were used to extend the sequence. If more than one extension is necessary or desired, additional sets of primers are designed to further extend the known region.

High fidelity amplification was obtained by following the instructions for the XL-PCR kit (Perkin-Elmer) and thoroughly mixing the enzyme and reaction mix. PCR was performed using the PTC-200 thermal cycler (MJ Research), beginning with 40 pmol of each primer and the recommended concentrations of all other components of the kit, with the following parameters:

| Step 1 | 94° C.. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat steps 4 through 6 for an additional 15 cycles |

| | |
|---|---|
| Step 8 | 94° C. for 15 sec |
| Step 9 | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 μl to 10 μl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQUICK (QIAGEN), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2 to 3 hours, or overnight at 16° C. Competent E. coli cells (in 40 μl of appropriate media) were transformed with 3 μl of ligation mixture and cultured in 80 μl of SOC medium. (See, e.g., Sambrook, supra, Appendix A, p. 2.) After incubation for one hour at 37° C., the E. coli mixture was plated on Luria Bertani (LB) agar (See, e.g., Sambrook, supra, Appendix A, p. 1) containing carbenicillin (2× carb). The following day, several colonies were randomly picked from each plate and cultured in 150 μl of liquid LB/2× carb medium placed in an individual well of an appropriate commercially-available sterile 96-well microtiter plate. The following day, 5 μl of each overnight culture was transferred into a non-sterile 96-well plate and, after dilution 1:10 with water, 5 μl from each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequences of SEQ ID NO:2, SEQ ID NO:4, are used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:2, SEQ ID NO:4, are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO™ 4.06 software (National Biosciences) and labeled by combining 50 pmol of each oligomer, 250 μCi of [γ-$^{32}$P] adenosine triphosphate (Amersham), and T4 polynucleotide kinase (DuPont NEN, Boston, Mass.). The labeled oligonucleotides are substantially purified using a SEPHADEX G-25 superfine size exclusion dextran bead column (Amersham Pharmacia Biotech). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba I, or Pvu II (DuPont NEN, NEN).

The DNA from each digest is fractionated on a 0.7% agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR film (Eastman Kodak, Rochester, N.Y.) is exposed to the blots to film for several hours, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE (DNASTAR). Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467–470; and Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the SCSH-encoding sequences, or any parts thereof, are used to detect, decrease, or inhibit expression of naturally occurring SCSH. Although use of oligonucleotides comprising from about 15 to 30 base pairs is described, essentially the same procedure is used with smaller or with larger sequence fragments. Appropriate oligonucleotides are designed using OLIGO 4.06 software (National Biosciences) and the coding sequence of SCSH. To inhibit transcription, a complementary oligonucleotide is designed from the most unique 5' sequence and used to prevent promoter binding to the coding sequence. To inhibit translation, a complementary oligonucleotide is designed to prevent ribosomal binding to the SCSH-encoding transcript.

IX. Expression of SCSH

Expression and purification of SCSH is achieved using bacterial or virus-based expression systems. For expression of SCSH in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21(DE3). Antibiotic resistant bacteria express SCSH upon induction with isopropyl beta-D-thiogalactopyranoside (IPTG). Expression of SCSH in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding SCSH by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. USA 91:3224–3227; Sandig, V. et al. (1996) Hum. Gene Ther. 7:1937–1945.)

In most expression systems, SCSH is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma japonicum*, enables the purification of fusion proteins on immobilized glutathione under conditions that maintain protein activity and antigenicity (Amersham Pharmacia Biotech). Following purification, the GST moiety can be proteolytically cleaved from SCSH at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (QIAGEN). Methods for protein expression and purification are discussed in Asubel, (1995; supra, ch 10, 16). Purified SCSH obtained by these methods can be used directly in the following activity assay.

X. Demonstration of SCSH Activity

The assay for human succinyl-CoA synthetase holoenzyme is based upon the release of reduced coenzyme A (CoASH) following cleavage of the thioester bond of succinyl-CoA to yield succinate and CoASH. SCSH activity in a sample is assayed by measuring production of CoASH. (Srere, P. A. (1969) Meth. Enzymol. 13:3–11.) The assay is carried out in an optical cuvette containing SCSH, 5,5'-dithiobis-(2-nitrobenzoate) (DTNB or Ellman's reagent), succinyl-CoA, GDP, inorganic phosphate, and water. CoASH reacts with DTNB to form a yellow-colored aromatic thiol. The amount of thiol formed is measured by absorption at 412 nm using a spectrophotometer and is proportional to the activity of SCSH in the sample.

XI. Functional Assays

SCSH function is assessed by expressing the sequences encoding SCSH at physiologically elevated levels in mammalian cell culture systems. cDNA is subcloned into a mammalian expression vector containing a strong promoter that drives high levels of cDNA expression. Vectors of choice include pCMV SPORT (Life Technologies) and pCR 3.1 (Invitrogen, Carlsbad, Calif., both of which contain the cytomegalovirus promoter. 5–10 $\mu$g of recombinant vector are transiently transfected into a human cell line, preferably of endothelial or hematopoietic origin, using either liposome formulations or electroporation. 1–2 $\mu$g of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP, Clontech), CD64, or a CD64-GFP fusion protein. Flow cytometry (FCM), an automated, laser optics-based technique, is used to identify transfected cells expressing GFP or CD64-GFP, and to evaluate properties, for example, their apoptotic state. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; downregulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) *Flow Cytometry*, Oxford, New York, N.Y.

The influence of SCSH on gene expression can be assessed using highly purified populations of cells transfected with sequences encoding SCSH and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success, N.Y.). mRNA can be purified from the cells using methods well known by those of skill in the art. Expression of mRNA encoding SCSH and other genes of interest can be analyzed by Northern analysis or microarray techniques.

XII. Production of SCSH Specific Antibodies

SCSH substantially purified using polyacrylamide gel electrophoresis (PAGE; see, e.g., Harrington, M. G. (1990) Methods Enzymol. 182:488–495), or other purification techniques, is used to immunize rabbits and to produce antibodies using standard protocols.

Alternatively, the SCSH amino acid sequence is analyzed using LASERGENE software (DNASTAR Inc.) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel (1995) supra, ch. 11.)

Typically, oligopeptides 15 residues in length are synthesized using an Applied Biosystems Peptide Synthesizer Model 431A using fmoc-chemistry and coupled to KLH (Sigma, St. Louis, Mo.) by reaction with N-maleimidobenzoyl-N-hydroxysuccinimide ester (MBS) to increase immunogenicity. (See, e.g., Ausubel (1995) supra.) Rabbits are immunized with the oligopeptide-KLH complex in complete Freund's adjuvant. Resulting antisera are tested for antipeptide activity by, for example, binding the peptide to plastic, blocking with 1% BSA, reacting with rabbit antisera, washing, and reacting with radio-iodinated goat anti-rabbit IgG.

XIII. Purification of Naturally Occurring SCSH Using Specific Antibodies

Naturally occurring or recombinant SCSH is substantially purified by immunoaffinity chromatography using antibodies specific for SCSH. An immunoaffinity column is constructed by covalently coupling anti-SCSH antibody to an activated chromatographic resin, such as CNBr-activated SEPHAROSE (Amersham Pharmacia Biotech). After the coupling, the resin is blocked and washed according to the manufacturer's instructions.

Media containing SCSH are passed over the immunoaffinity column, and the column is washed under conditions that allow the preferential absorbance of SCSH (e.g., high ionic strength buffers in the presence of detergent). The column is eluted under conditions that disrupt antibody/SCSH binding (e.g., a buffer of pH 2 to pH 3, or a high concentration of a chaotrope, such as urea or thiocyanate ion), and SCSH is collected.

XIV. Identification of Molecules Which Interact with SCSH

SCSH, or biologically active fragments thereof, are labeled with $^{125}I$ Bolton-Hunter reagent. (See, e.g., Bolton et al. (1973) Biochem. J. 133:529.) Candidate molecules previously arrayed in the wells of a multi-well plate are incubated with the labeled SCSH, washed, and any wells with labeled SCSH complex are assayed. Data obtained using different concentrations of SCSH are used to calculate values for the number, affinity, and association of SCSH with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide encoding the polypeptide comprising an amino acid sequence selected from the group consisting of SEQ ID NO:1 and SEQ ID NO:2.

2. An isolated and purified polynucleotide which hybridizes under stringent conditions to the polynucleotide of claim 1.

3. An isolated and purified polynucleotide having a sequence which is complementary to the polynucleotide sequence of claim 1.

4. An isolated and purified polynucleotide comprising a polynucleotide sequence selected from the group consisting of SEQ ID NO:2 and SEQ ID NO:4.

5. An isolated and purified polynucleotide having a sequence which is complementary to the polynucleotide of claim 4.

6. An expression vector comprising at least a fragment of the polynucleotide of claim 1.

7. A host cell comprising the expression vector of claim 6.

8. A method for producing a polypeptide comprising the amino acid sequence selected from the group consisting of SEQ ID NO:1 and SEQ ID NO:3, the method comprising the steps of:
   a) culturing the host cell of claim 7 under conditions suitable for the expression of the polypeptide; and
   b) recovering the polypeptide from the host cell culture.

9. A method for detecting a polynucleotide encoding the polypeptide comprising the amino acid sequence selected from the group consisting of SEQ ID NO:1 and SEQ ID NO:3, in a biological sample, the method comprising the steps of:
   (a) hybridizing the polynucleotide of claim 3 to at least one of the nucleic acids in the biological sample, thereby forming a hybridization complex; and
   (b) detecting the hybridization complex, wherein the presence of the hybridization complex correlates with the presence of the polynucleotide encoding the polypeptide in the biological sample.

10. The method of claim 9 further comprising amplifying the polynucleotide prior to hybridization.

* * * * *